United States Patent [19]

Beavers

[11] Patent Number: 4,663,233

[45] Date of Patent: May 5, 1987

[54] LENS WITH HYDROPHILIC COATING

[75] Inventor: Ellington M. Beavers, Meadowbrook, Pa.

[73] Assignee: Universal High Technologies, Dobbs Ferry, N.Y.

[21] Appl. No.: 791,021

[22] Filed: Oct. 24, 1985

[51] Int. Cl.$^4$ ............................. A61F 1/16; A61F 1/24
[52] U.S. Cl. .................... 428/412; 428/424.2; 427/164; 427/165; 350/409; 350/444
[58] Field of Search ............... 350/409, 444; 427/164, 427/165; 428/412, 424.2

[56] References Cited

U.S. PATENT DOCUMENTS

| | | | |
|---|---|---|---|
| 3,882,036 | 5/1975 | Krezanoski et al. | 252/106 |
| 3,884,826 | 5/1975 | Phares, Jr. et al. | 252/106 |
| 3,954,644 | 5/1976 | Krezanoski et al. | 252/106 |
| 4,038,421 | 7/1977 | Mendy et al. | 426/72 |
| 4,046,706 | 9/1977 | Krezanoski et al. | 252/106 |
| 4,060,081 | 11/1977 | Yannas et al. | 128/156 |
| 4,141,973 | 2/1979 | Balazs | 424/180 |
| 4,146,603 | 3/1979 | Hummelstown | 424/1 |
| 4,152,212 | 5/1979 | Pope et al. | 195/66 |
| 4,169,866 | 10/1979 | Hertman et al. | 260/823 |
| 4,172,128 | 10/1979 | Thiele et al. | 614/15 |
| 4,174,389 | 11/1979 | Cope | 424/94 |
| 4,178,285 | 12/1979 | Felts et al. | 260/112 R |
| 4,178,361 | 12/1979 | Cohen et al. | 424/22 |
| 4,195,097 | 3/1980 | Stekolnikov et al. | 426/61 |
| 4,211,769 | 7/1980 | Okada et al. | 424/177 |
| 4,240,163 | 12/1980 | Galin | 3/13 |
| 4,264,155 | 4/1981 | Miyata | 351/160 |
| 4,264,576 | 4/1981 | Zimmerman et al. | 424/22 |
| 4,264,577 | 4/1981 | Zimmerman et al. | 424/22 |
| 4,264,589 | 4/1981 | Felts et al. | 424/99 |
| 4,272,522 | 6/1981 | Balazs | 424/94 |
| 4,280,954 | 7/1981 | Lexington et al. | 260/123.7 |
| 4,286,062 | 8/1981 | Stekolnikov et al. | 435/188 |
| 4,296,104 | 10/1981 | Herschler | 424/153 |
| 4,296,130 | 10/1981 | Herschler | 424/337 |
| 4,303,676 | 12/1981 | Balazs | 424/359 |
| 4,322,523 | 3/1982 | Wagner | 536/4 |
| 4,328,803 | 5/1982 | Pape | 128/276 |
| 4,341,869 | 7/1982 | Langer et al. | 435/232 |
| 4,365,050 | 12/1982 | Ivani | 527/312 |
| 4,369,256 | 1/1983 | Caso | 521/25 |
| 4,370,353 | 1/1983 | Yagi et al. | 426/570 |
| 4,373,023 | 2/1983 | Langer et al. | 435/2 |
| 4,379,839 | 4/1983 | Spiegelman | 435/5 |
| 4,459,317 | 7/1984 | Lambert | 427/2 |
| 4,487,865 | 12/1984 | Balazs et al. | |
| 4,500,676 | 2/1985 | Balazs et al. | |

OTHER PUBLICATIONS

*The Wall Street Journal*, Friday, Jun. 29, 1984, art. entitled "Lens Implants for Cataracts are Offering More Protection", para. 9.

Astra Meditec AG: PCT/SE83/00191: WO83/03977–'Articles Exhibiting a Biocompatible Surface Layer and Process for Providing Articles with Such a Surface Layer".

*Primary Examiner*—John Kight
*Assistant Examiner*—M. L. Moore
*Attorney, Agent, or Firm*—David H. Semmes; Warren E. Olsen

[57] ABSTRACT

Optical lenses, particularly spectacle, contact and intraocular lenses manufactured from glass or plastic. The lenses are provided with a hydrophilic coating which is immobilized upon the lens to provide permanent lubricity and uniform wetting characteristics.

12 Claims, No Drawings

LENS WITH HYDROPHILIC COATING

CROSS-REFERENCES TO RELATED APPLICATIONS

An improvement upon METHOD OF HYDROPHILIC COATING OF PLASTICS (Ser. No. 643,598) filed by applicant and co-inventors on Aug. 23, 1984.

BACKGROUND OF THE INVENTION

1. Field of the Invention

Optical lenses, manufactured from glass or plastic and provided with an hydrophilic coating. The hydrophilic coating is immobilized upon the plastic to provide lubricity and uniform wetting characteristics.

2. Description of the Prior Art

KREZANOSKI et al., U.S. Pat. No. 3,882,036;
PHARES JR. et al., U.S. Pat. No. 3,884,826;
KREZANOSKI et al., U.S. Pat. No. 3,954,644;
KREZANOSKI et al., U.S. Pat. No. 4,046,706;
ALAZS, 4,141,973;
GALIN, 4,240,163;
MIYATA, 4,264,155;
IVANI, 4,365,050.

Applicant's comments upon these patents are being submitted separately in an Information Disclosure Statement.

SUMMARY OF THE INVENTION

According to the present invention, lenses, such as "hard" or "soft" contact lenses as well as intra-colour lenses are provided with an immobilized hydrophilic coating. A matrix in the form of an acrylic copolymer film is cured upon the clear lens base so as to react chemically with a polysaccharide. Then a polysaccharide coating is cross-linked by chemical reaction with the copolymer film, so as to be substantially insoluble and immobile. The result is an hydrophilic coating which is highly lubricious and is permanently immobilized upon the matrix.

DESCRIPTION OF THE PREFERRED EMBODIMENTS

It is well known that the so-called "hard" plastic contact lens, made from polymethyl methacrylate, for example, can be made to correct the natural defects of eyesight and permit excellent vision. However, the lenses are often uncomfortable to wear for more than short periods, and some people cannot tolerate the discomfort at all. The "soft" lens was invented to alleviate this problem, and indeed hydrophilic lenses swollen with water can in many cases be tolerated for long periods of up to several days. However, an important penalty paid for improved comfort is less precise correction of the defect in visual acuity—the patient can't see as well with the soft lens.

According to the present invention, both comfort and sharpness of vision are provided in a lens. The hard lens can be made comfortable by coating it entirely or optionally on the rim only with a hydrophilic system that is insoluble, immobile, and inert. The same new hydrophilic system can be coated on the intra-ocular lens designed to be inserted surgically in place of the natural lens which may have become clouded or diseased.

It is common for the surgeon to apply an aqueous solution of sodium hyaluronate to the wound during the insertion of the intra-ocular lens, to reduce pain and facilitate healing. However, because the material is soluble and can be washed away, it remains only temporarily and its effect is quickly lost. The surface of applicant's coated lens is equally lubricious and the effect is permanent because of the immobility of the polysaccharide moiety tied chemically to the coating matrix.

OPERATIONAL DESCRIPTION

The hydrophilic coating of this invention is applied by any of several processes, as will be described, and essential features are (1) that the coating must comprise a minimum of two quite different strata capable of mutual interaction chemically, and (2) that the final composite coating is cross-linked, insoluble, and immobile. For convenience of discussion, the top coat will be called the "hydrophil" and the underlying coat or coats will be known collectively as the "matrix".

The matrix is a film-forming polymer, copolymer, or mixture of polymers, copolymers and/or reactants and solvents. At least one component of the matrix must be capable of chemical reaction with the polysaccharide component of the hydrophil. The matrix must also show excellent adhesion to the structure being coated, both before and after conversion to its cross-linked state. For obvious reasons, the cross-linked coating must be clear and transparent, essentially colorless except as dyes may have been added, and free of particulate matter.

As will be apparent, the chemical system developed for the matrix depends in part on the nature of the object to be coated. For coating plastics such as polymethyl methacrylate, polycarbonate, or polysiloxane, acrylic systems are generally excellent choices.

For coating glass, epoxy systems are better for retention of adhesion after long exposure of the coated object to water. In a preferred embodiment of this invention, a thermosetting epoxy resin film is first applied to the glass and partially cured. An acrylic copolymer containing hydroxyl or epoxy groups is then applied and the article further heated. Finally, the hydrophil coat is added and curing then completed. Articles coated in this manner may be immersed in water for long periods without signigicant loss of adhesion or integrity of the coating.

The hydrophil portion of the composite coating will normally be a polysaccharide, such as hyaluronic acid, agarose, chondroitin sulfate, or the like. Salts of such polysaccharides are normally the form isolated from the common natural sources, such as rooster comb, umbilical cord, or submerged culture with appropriate microorganisms. The salts can be used as such, but adjustments in concentration may be necessary to accommodate the particular salt of choice. For example, sodium hyaluronate will normally be applied at a concentration of less than 1% in water, whereas potassium hyaluronate will be applied at a concentration of 1% or more.

Applicant has provided methods for applying coatings to the surfaces of both contact and intra-ocular lenses. In coating only the rim of a contact lens, a preferred technique is to apply the wet coating solution at carefully controlled thickness onto plate glass or other plane surface and then to dip the edge of the contact lens (concave side downward) briefly into the wet film, making sure that the lens is held so that the plane of the downward edge is parallel to the plane of the surface bearing the wet coating. A simple jig can be designed to pick up the lens with a rubber suction cup from a dry area of the surface, swing it over the wet area, and lower it vertically into the wet film. The lens holder then rotates 180 degrees to allow the edge-coated lens to be transferred to an oven for curing. The desired number of coats or chosen compositions may be applied in this manner.

The thickness of the wet film on the flat surface determines the distance inward from the edge that the lens is coated. Similarly, the thickness of the coating on the lens edge is determined by the concentration of the solution and by the number of coats applied.

When the entire contact or intra-ocular lens is to be coated, a preferred technique may be to hold the lens with a three-prong grip made of wire of very fine gauge from a non-corroding metal. The lens thus held is dipped into the chosen coating solutions and then spun at controlled speed to throw off excess solution and to ensure surfaces of optical quality showing no flow marks or beads. The coating is then cured as necessary. In such manner, coatings can be made with uniform and controlled thickness from as low as a few microns to as high as several thousandths of an inch or more.

It is extremely important, of course, that the coated lenses be chemically inert and physically stable in the environment of the eye, so that they impart no extractable substance that might be harmful and do not delaminate or throw off flakes or other particles due to degradation of the coating. Tests made under conditions of exaggerated stress have confirmed the inertness and integrity of lenses coated with properly chosen materials under properly controlled conditions.

EXAMPLE 1: [B-115 (50%)]

A 1,000-ml three-neck round-bottom flask was fitted with a thermometer, an agitator, a water-cooled condenser, and a dropping funnel. Ethylene glycol monoethyl ether acetate (Cellosolve acetate), 368 g., was charged to the flask and stirring and heating started. When the temperature of the liquid reached 100 degrees C., heat input was adjusted to hold the temperature for the remainder of the run at 100 degrees and the dropwise addition of the following monomer-catalyst mixture was started:

| Ethyl methacrylate | 333.8 g. |
|---|---|
| Hydroxyethyl methacrylate | 31.2 |
| Methacrylic acid | 2.8 |
| t-Butyl peroctoate | 0.92 |
| Mercaptoethanol | 0.36 |

Addition of the monomer-catalyst mix was complete after one hour, and heating and stirring were continued for one more hour at 100 degrees.

The batch was then cooled to room temperature and filtered. The product, designated B-1115 (50%), was viscous, sparkling clear and colorless.

EXAMPLE 2: [B-205 (50%) and B-229 (60%)]

In essentially the same manner were prepared the products designated B-205 (50%) and B-229 (60%), also clear, viscous solutions. The two polymer products were characterized by having the following mole-ratios of monomer constituents:

| B-205 | 90/7.5/2.5 EMA/HEMA/MAA |
|---|---|
| B-229 | 80.5/19.3/0.2 EMA/HEMA/MAA |

EXAMPLE 3: [Mix A (For Glass) and Mix B (For Plastics)]

With the polymer solutions described in Examples 1 and 2, films of various controlled thicknesses were prepared on glass plates, and on flat panels made of polymethyl methacrylate, polycarbonate, and polysiloxane. Considerations of solubility, flow and leveling, and drying time at 65 degrees C. in a vacuum oven, as well as adhesion of the dried film to the substrate, led to preferred formulations for each substrate, such as the following:

Mix A (for glass)

| B-229 (60%) | 46.7 g. |
|---|---|
| B-205 (50%) | 18.3 |
| Desmodur N (75%) (an aliphatic polyisocyanate) | 11.8 |
| Methoxyethyl acetate | 8.3 |
| Xylenes | 14.8 |

Mix B (for plastics)

| B-229 (60%) | 46.7 g. |
|---|---|
| B-1115 (50%) | 18.3 |
| Desmodur N (75%) (an aliphatic polyisocyanate) | 11.8 |
| Methoxyethyl acetate | 8.3 |
| Xylenes | 14.8 |

The wet coated panels were placed in a vacuum oven at 65 degrees C. and 20 inches of vacuum for 25 minutes. After being cooled to room temperature, a coat of 1% solids aqueous potassium hyaluronate was applied at a nominal thickness of 3 mils on each panel. The panels were returned to the oven and cured under the same conditions as earlier, for two hours. When cooled and washed with tap water, the coatings were observed to be permanently slippery when wet with water, and clear and non-tacky when dry. Droplets of water thrown onto the panels did not collect in beads, but spread uniformly over the surface, causing no distortion of light passing through the panels.

EXAMPLE 4: [B-253]

Into a three-neck flask equipped with stirrer, thermometer, condenser and dropping funnel were charged 227.5 g. of PM acetate (propylene glycol monomethyl ether acetate) and 122.5 g. of mixed xylenes. The mixture was heated to 100 degrees C. and dropwise addition of the following solution was begun:

| Ethyl methacrylate | 273.8 g. |
|---|---|
| Hydroxyethyl methacrylate | 75.6 |
| Methacrylic acid | 0.7 |
| t-Butyl peroctoate | 1.1 |
| Mercaptoethanol | 0.42 |

When all the solution had been added, heating was continued for another hour at 100 degrees C. and the product then cooled to room temperature and labeled B-253. It was viscous, clear and colorless.

EXAMPLE 5—(Mix C)

The following mix was prepared:

Mix C

| | |
|---|---|
| B-253 | 25 g. |
| B-1115 | 15 |
| Acryloid U-608S (an acrylic copolymer containing hydroxyl groups) | 25 |
| Desmodur N-3390 (an aliphatic polyisocyanate) | 35 |
| PM acetate | (To dilute to 50% solids) |

Acryloid U-608S is a product of Rohm and Haas Company. Desmodur N-3390 is a product of Mobay Chemical Company.

A 5-mil wet film of Mix C was applied by knife to plate glass and a clean, dry, acrylic contact lens was lowered concave-down into the film until it came to rest on the glass. (Care was exercised to ensure that the lens was lowered in a line exactly vertical to the plane of the glass plate, by use of the jig described in the foregoing discussion of this specification.) The lens was immediately removed from the wet film and cured for 25 minutes at 65 degrees C. under 20 inches of vacuum. The dipping operation was then repeated, except that the wet film was a 1% aqueous solution of potassium hyaluronate. The lens was then cured for two hours at 65 degrees C. under 20 inches of vacuum, washed thoroughly with water, and stored in normal saline solution.

Alternatively, the uncoated contact lens was held by a fine wire tricept and coated by dipping into containers of Mix C and of 1% potassium hyaluronate, each coat being followed by spinning to remove excess solution, and curing as described above.

EXAMPLE 6

The coated polyMMA panel described in Example 3 was sawed into pieces one-half of one inch in size and immersed in 150 grams of distilled water contained in a round-bottom flask fitted with water-cooled condenser. The flask was heated until the water boiled, and boiling under reflux was continued for twenty-four hours. When cold, the water was decanted into a weighed evaporating dish and the dish placed in an oven at 105 degrees C. When the water had all evaporated, the dish was reweighed and found to contain no extract. The plastic samples were examined and found to show no delamination of the coating; the coated surface was still lubricious and shed water droplets without beading. No property of the samples was found to have changed as a result of the 24-hour boil in water.

Contact lenses completely coated as described in Example 4 were mounted convex side up on the perimeter of a wheel and a camel's hair brush fixed beside the wheel in such position that the surface of the lens was brushed with each revolution of the wheel. After 200,000 such strokes, the lens was unaffected; clarity and appearance were unchanged, and the lubricity of the surface had also not been affected.

EXAMPLE 7

A 10-mil wet film of Epi-Rez 509, an ether of bis phenol product of The Celanses Company, was catalyzed with five weight percent benzyldimethylamine was knifed onto a glass plate and baked at 115 degrees C. for 2 hours. At the end of this time, the cooled film was hard and faintly tacky. Over this coat was applied a 6-mil wet film of Mix C, and the panel was returned to the oven for 25 minutes at 65 degrees C. A third coat was then applied, consisting of a 1% aqueous solution of potassium hyaluronate. Finally, the panel was baked for two hours at 65 degrees C.

The final film was dry, clear and free of optical distortion; when wet with water, the surface was lubricious and remained so after long rubbing under a stream of tap water. When soaked in water for 24 hours or more, adhesion of the coating to glass remained excellent.

I claim:
1. A lens with hydrophilic coating comprising:
   (a) a clear lens base;
   (b) a matrix in the form of an acrylic copolymer film cured by partial reaction with a polyisocyanate capable of reacting chemically also with a polysaccharide; and
   (c) a polysaccharide coating cross-linked by chemical reaction with said copolymer film so as to be substantially insoluble and immobile.
2. A lens with hydrophilic coating as in claim 1, wherein said lens base is plastic.
3. A lens with hydrophilic coating as in claim 1, wherein said lens base is glass.
4. A lens with hydrophilic coating as in claim 1, wherein said polysaccharide is a salt of hyaluronic acid.
5. A lens with hydrophilic coating as in claim 1, wherein said polysaccharide is agarose.
6. A lens with hydrophilic coating comprising:
   (a) a clear lens base;
   (b) a matrix affixed to said base in the form of a polymer film made from monomers including:
      (i) EMA/HEMA/MAA
      (ii) Desmodur N
      (iii) ethylene glycol monoethyl ether acetate
      (iv) Xylenes and
   (c) a polysaccharide cross-linked by chemical reaction with said polymer film so as to be substantially insoluble and immobile.
7. A lens with hydrophilic coating as in claim 6, wherein the monomers are in the following approximate proportions:

| | | |
|---|---|---|
| (i) | EMA/HEMA/MAA | 46.7 |
| (ii) | EMA/HEMA/MAA | 18.3 |
| (iii) | Desmodur N | 11.8 |
| (iv) | Methoxyethyl acetate | 8.3 |
| (v) | Xylenes | 14.8 |

8. A lens with hydrophilic coating comprising:
   (a) a clear plastic lens base;
   (b) a matrix affixed to said base in the form of an acrylic copolymer film, including:
      (i) a mix of: Ethyl methacrylate Hydroxyethyl methacrylate Methacrylic acid t-Butyl peroctoate Mercaptoethanol
      (ii) Desmodur N
      (iii) Methoxyethyl acetate
      (iv) Xylenes and
   (c) a polysaccharide coating formed from 1% solids aqueous sodium hyaluranate cross-linked by chemical reaction with said acrylic copolymer film so as to be substantially insoluble and immobile.
9. A lens with hydrophilic coating as in claim 8, wherein the monomers are in the following approximate proportions:

(i) a mix of: Ethyl methacrylate Hydroxyethyl methacrylate Methacrylic acid t-Butyl peroctoate Mercaptoethanol 46.7 g.
(ii) Desmodur N 11.8
(iii) Methoxyethyl acetate 8.3
(iv) Xylenes 14.8.

10. A lens with hydrophylic coating comprising:
(a) a clear lens base;
(b) a matrix in the form of an acrylic copolymer film affixed to said base and including:
Ethyl methacrylate 273.8 g.
Hydroxyethyl methacrylate 75.6
Methacrylic acid 0.7
t-Butyl peroctoate 1.1
Mercaptoethanol 0.42 and
(c) a polysaccharide coating formed from 1% sodium hyaluronate.

11. A lens with a hydrophilic coating comprising:
(a) a clear glass lens base;
(b) a matrix film affixed to said base in the form of:
(i) 10 mil wet film of an epoxy resin and 5% benzyldimethylamine baked onto said plate;
(ii) A mixture of: Ethyl methacrylate Hydroxyethyl methacrylate Methacrylic acid t-Butyl peroctoate Mercaptoethanol 40 g.
(iii) An acrylic copolymer containing hydroxyl groups 25 g.
(iv) Desmodur N 35 g.
(v) Propylene glycol monomethyl ether acetate (to dilute to 50% solids); and
(c) a polysaccharide coating applied in the form of 1% aqueous solution of sodium hyaluronate and then cross-linked by chemical reaction with said matrix so as to be substantially insoluble and immobile.

12. A lens with a hydrophilic coating as in claim 11, wherein the monomers are in the following approximate proportions:
(i) 10 mil wet film of an epoxy resin and 5% benzyldimethylamine baked onto said lens;
(ii) a mixture of: Ethyl methacrylate Hydroxyethyl methacrylate Methacrylic acid t-Butyl peroctoate Mercaptoethanol 25 g.
(iii) A mixture of: Ethyl methacrylate Hydroxyethyl methacrylate Methacrylic acid t-Butyl peroctoate Mercaptoethanol 15 g.
(iv) Acryloid U-608S 25 g.
(v) Desmodur N-3390 35 g.
(vi) Propylene glycol monomethyl ether acetate (to dilute to 50% solids).

* * * * *